United States Patent
Hillyard

(10) Patent No.: US 9,295,610 B1
(45) Date of Patent: Mar. 29, 2016

(54) OZONE GENERATOR FITTING

(71) Applicant: Waterway Plastics, Oxnard, CA (US)

(72) Inventor: Jason Hillyard, Oxnard, CA (US)

( * ) Notice: Subject to any disclaimer, the term of this patent is extended or adjusted under 35 U.S.C. 154(b) by 121 days.

(21) Appl. No.: 14/336,543

(22) Filed: Jul. 21, 2014

(51) Int. Cl.
| | |
|---|---|
| *E03D 9/02* | (2006.01) |
| *A61H 33/02* | (2006.01) |
| *A47K 3/00* | (2006.01) |
| *A61H 33/00* | (2006.01) |
| *A61L 2/20* | (2006.01) |

(52) U.S. Cl.
CPC ............... *A61H 33/02* (2013.01); *A47K 3/001* (2013.01); *A61H 2033/0016* (2013.01); *A61L 2/202* (2013.01)

(58) Field of Classification Search
CPC ..................................................... A61H 33/02
USPC ........................................ 4/222, 541.1–541.5
See application file for complete search history.

(56) References Cited

U.S. PATENT DOCUMENTS

| | | | | |
|---|---|---|---|---|
| 4,995,123 | A * | 2/1991 | Kern .......................... | C02F 1/78 137/563 |
| 6,357,060 | B2 * | 3/2002 | Gloodt ...................... | A47K 3/10 210/764 |
| 6,405,387 | B1 * | 6/2002 | Barnes ............... | A61H 33/0087 4/541.1 |
| 8,095,998 | B2 * | 1/2012 | Lau ........................ | A61H 33/02 4/492 |
| 2003/0200604 | A1 * | 10/2003 | Loyd ........................ | C02F 1/78 4/541.5 |
| 2010/0176521 | A1 * | 7/2010 | Cunningham ............ | C02F 1/78 4/541.5 |

\* cited by examiner

Primary Examiner — Huyen Le

(57) ABSTRACT

A novel fitting for air blowers in air baths that is to be used in conjunction with the blower plumbing system between the blower and the mandated water backflow prevention safety device. The fitting has an internal structure that acts through a dual push/pull effect in order to divert a portion of the air through an ozone generator. The influent side acts as an air ram, like a pitot tube while the effluent side acts as a venturi. The design is symmetrical in that the fitting can be installed in either direction, i.e., the fitting is reversible in relation to the blower.

2 Claims, 3 Drawing Sheets

OZONE GENERATOR FITTING

BACKGROUND OF THE INVENTION

1. Field of the Invention

The present invention relates generally to the field of fittings for air bath tubs and more specifically toward a fitting that can easily and economically incorporate an ozone generator into the blower plumbing system for sanitation.

2. Description of the Prior Art

Typically, in an air bath tubs a blower is used to inject air bubbles into the water. Ozone generators are commonly used in water pump driven whirlpool bath plumbing systems, but ozone generators have had limited success in air bath systems. Ozone is a powerful oxidizing agent, far stronger than oxygen. It is also unstable at high concentrations, decaying to ordinary diatomic oxygen. It is used industrially for many applications, but for purpose of the instant application, it is to be used for killing microorganisms in air and water sources.

One example of a prior art system is the addition of pressurized air from the blower through an ozone generator and into the bath tub through an air injector fitting. This type of system does not treat the plumbing system with ozone however.

A second prior art example is when an ozone generator is connected to the inlet of a blower to pull the ozone through the plumbing system and into the bath. This method has serious drawbacks, however, as the heat generated by the blower motor, and heater on certain blowers, reduces the half-life of the ozone.

In a third prior art example, an ozone generator is coupled with an air pump to pressurize the ozone in order to induce it into the blower plumbing. The main drawbacks to this system are the cost of the air pump and the unpleasant noise it generates.

It is the object of the present invention to provide a fitting that can be attached between the blower and the water backflow prevention, device that has a higher degree of success of sanitizing the water through the generation of ozone than has been found in prior art systems and that overcomes the other limitations of the prior art.

SUMMARY OF THE INVENTION

The preferred embodiment of the present invention teaches a system for introducing ozone into a blower plumbing system comprising: a vessel containing water to receive injected air; plumbing to disperse said air connected to said vessel; a blower that injects air to said plumbing; a backflow prevention device between said manifold and said blower that prevents flow from returning to said blower; a fitting placed between said blower and said backflow device that introduces ozone to be injected with said air, said fitting further comprising: a first side attachable to said blower; a second side attachable to said backflow prevention device; a center cylinder having an outer surface and an interior hollow portion between said first side and said second side; a first hollow barb attached to said outer surface of said center cylinder; a second hollow barb attached to said outer surface of said center cylinder wherein said first barb is proximate said first side and said second barb is proximate said second side and wherein said first barb and said second barb are oriented substantially perpendicular to said center cylinder; an impeding structure centered between said first hollow barb and said second hollow barb in the interior hollow portion of said center cylinder; influent tubing attached to said first hollow barb; effluent tubing attached to said second hollow barb wherein said influent tubing and said effluent tubing attaches to an ozone generator thereby allowing said air to travel through said blower and perpendicular through said first barb into said ozone generator and back down through said effluent tubing into said second barb, through said backflow prevention device, through said plumbing into said vessel.

The above embodiment can be further modified by defining that said fitting further comprises: a first internal conduit inside said center cylinder extending from said first side wherein said first internal conduit has a diameter smaller than said center cylinder and wherein said first internal conduit carries influent up said first hollow barb; a second internal conduit inside said center cylinder extending toward said second side wherein said second internal conduit has a diameter smaller than said center cylinder and wherein said second internal conduit carries effluent from said second hollow barb.

DETAILED DESCRIPTION OF A PREFERRED EMBODIMENT

Figure 1:
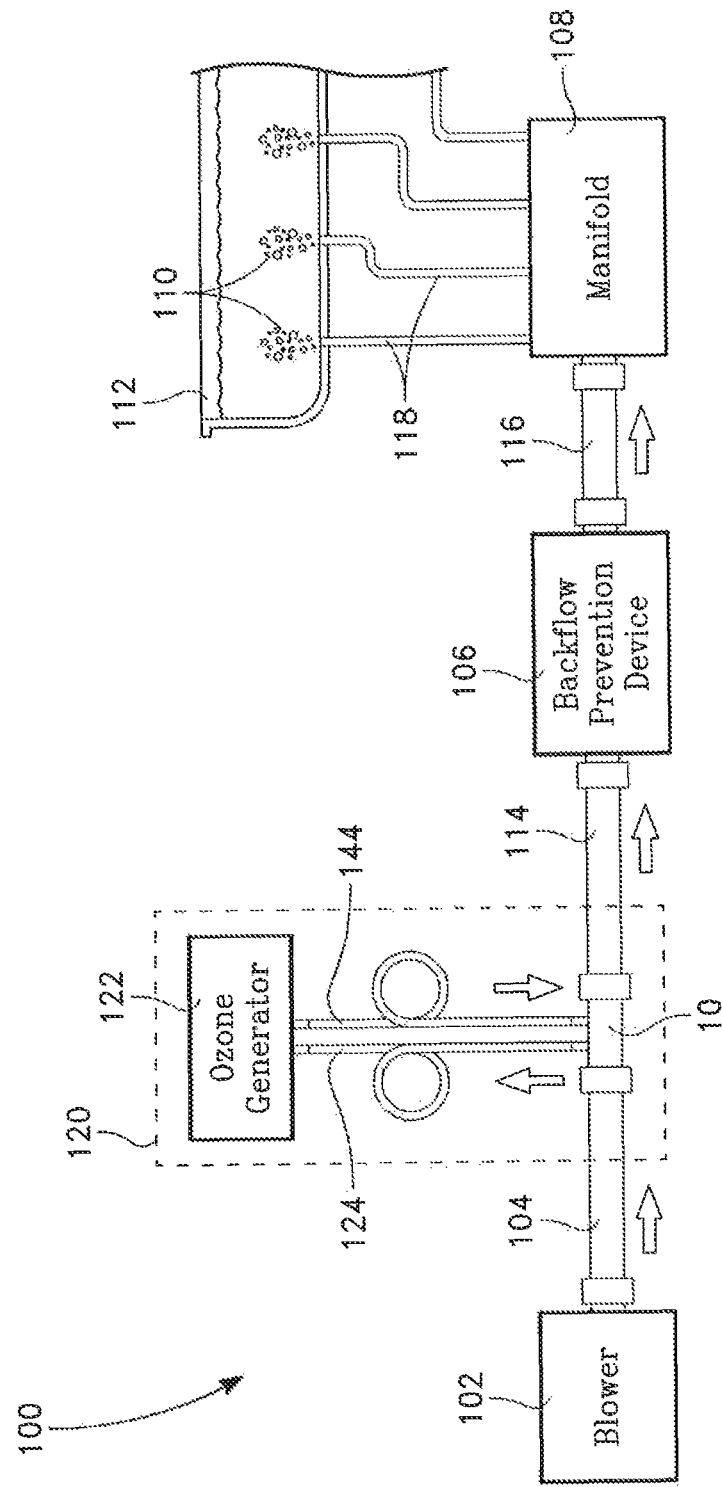
FIG. 1 is a schematic diagram of the fitting and system of the instant invention.

Turning to the drawings, the preferred embodiment is illustrated and described by reference characters that denote similar elements throughout the several views of the instant invention.

The preferred embodiments of the instant invention is illustrated in detail in FIGS. 1-6. FIG. 1 schematically shows the system 100 of the instant invention, which integrally involves the use of a novel fitting 10 that is to be used in conjunction with the blower plumbing system between the blower 102 and the mandated water backflow prevention safety device 106. The fitting 10 has an internal structure that is more closely detailed in FIG. 4 that acts through a dual push/pull effect in order to divert a portion of the air through an ozone generator. The influent side acts as an air ram, like a pitot tube while the effluent side acts as a venturi. The system design 100 is symmetrical in that the fitting 10 can be installed in either direction, the fitting 10 is reversible in relation to the blower 102. Because of this symmetry, we define the influent side 124 as the side proximate the blower 102 and the effluent side 144 as the side distal the blower 102 and proximate the backflow prevention safety device 106.

FIG. 1 shows the fitting 10 in relation to the blower 102 that is external to the tub 112 itself. The blower 102 has the fitting 10 attached to the blower 102 through a conduit fitting 104. The fitting 10 itself is attached to an ozone generator 122 through the bypass structure 120 that has tubing with an influent side 124 and an effluent side 144 thereby creating the ozone sanitation system that operates through the bypass structure 120. The fitting 10 then attaches to a second conduit fitting 114 where the air and ozone flows therefrom and into the mandated backflow prevention safety device 106. A third conduit fitting 116 moves the air and ozone from the backflow prevention safety device 106 and into a manifold 108, which then divides and disperses the air and ozone through a plurality of conduits 118 wherein the air and ozone 110 appear inside of the tub 112.

Figure 2:
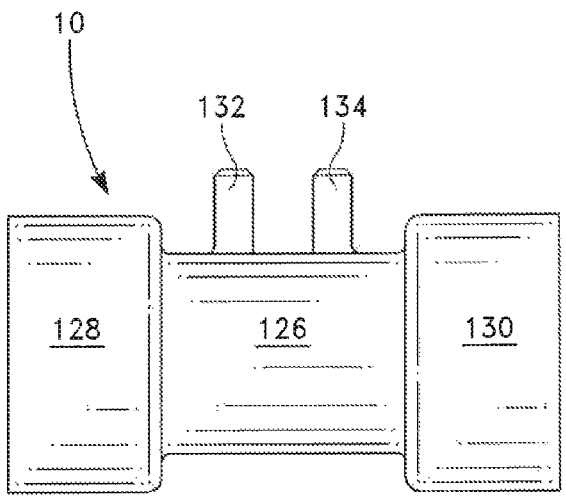
FIG. 2 is a side view of the fitting of the instant invention.
Figure 3:
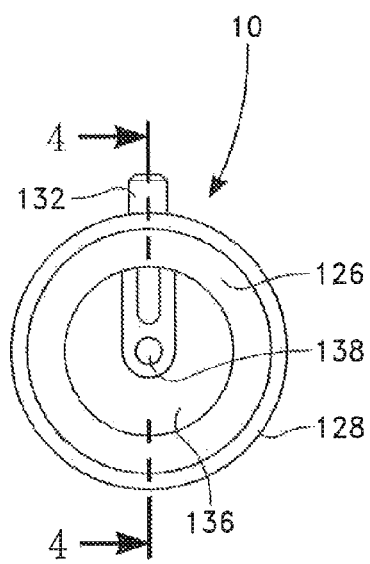
FIG. 3 is a view through the internal portion of the fitting of the instant invention.
Figure 4:
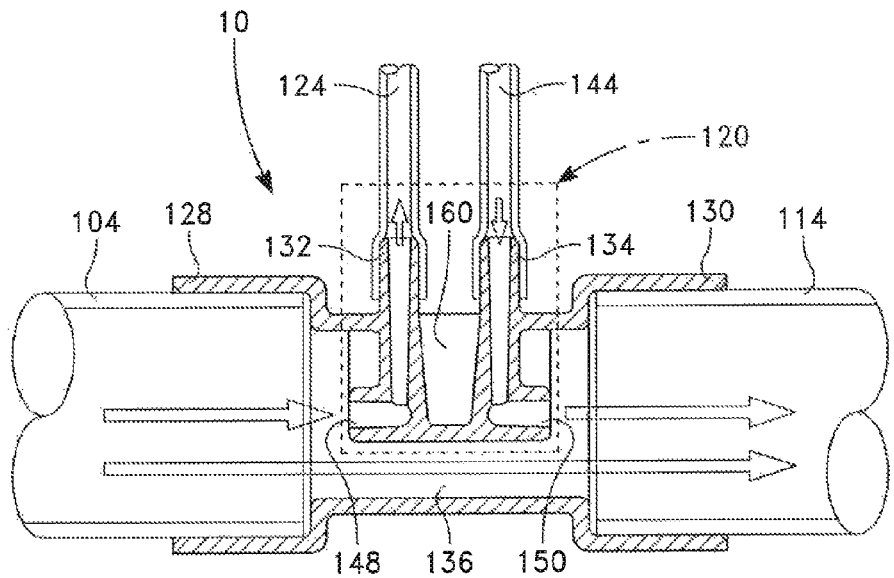
FIG. 4 is taken along the line 4-4 in FIG. 3 as an internal view of the workings of the system of the instant invention.

As seen in FIGS. 2-4, the fitting 10 has a cylindrical body 126 with attachment sleeves 128, 130 on either side. The cylindrical body 126 is hollow as seen in FIG. 3 to allow for the flow of air and ozone therethrough. Two hollow barbs 132, 134 extend from the cylindrical body 126 and into the internal cavity 136. The first barb 132 terminates in an aperture 138. The second barb 134 terminates in a similar aperture as shown in FIG. 3 but which is not shown. The barbs 132, 134 include hollow chambers therethrough so that air and ozone can enter into the internal chamber 136 of the fitting.

As seen in FIG. 4, influent tubing 124 and effluent tubing 144 are attached to the two hollow barbs 132, 134. Air is pushed through the blower 102, through the conduit 104, into the fitting 10 up the first flange 132 through a first tube 148 and through the first flange 132 that has an internal opening that intersects the first tube 148. At least some portion of air flows through the influent tubing 124 and into the ozone generator 122, which then passes the effluent ozone treated air from the ozone generator through effluent tubing 144 back through the second flange 134 that has an internal opening that intersects a second tube 150 into the hollow center 136 of the cylindrical body 126.

The diameter of the cylindrical body 126 is sized relative to the air flow of the blower to maintain a sufficient velocity through which the internal cavity 136 at the bypass structure 120. The bypass structure 120 includes the influent tube 148 and the effluent tube 150 and both tubes 148, 150 are parallel to the cylindrical body 126 and located within the cylindrical body 126. The narrowed flow through these tubes creates impedance to the main air flow.

Figure 5:
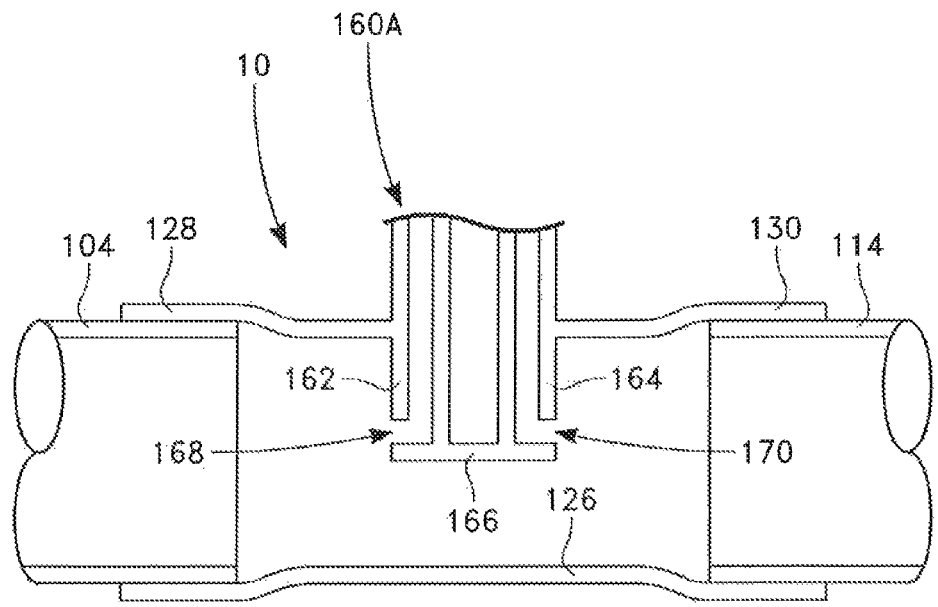
FIG. 5 is a close up view of one embodiment of the impedance between the two barbs.
Figure 6:
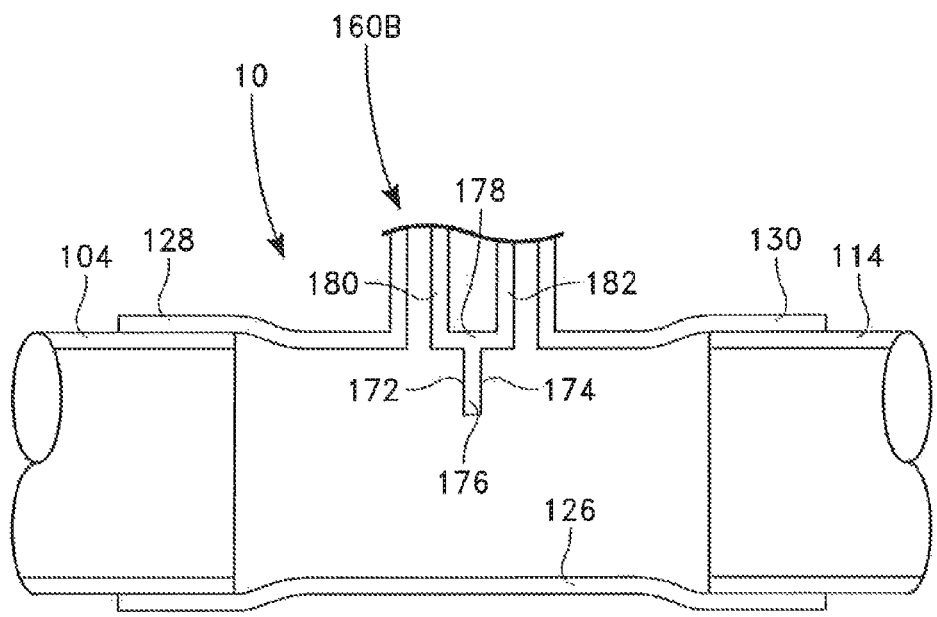
FIG. 6 is a close view of an alternate embodiment of the impedance between the two barbs.

The impedance structure 160 is shown in close-up in FIGS. 5 and 6. In the preferred embodiment 160A shown in FIG. 5, as the air flow moves from the first side 104 into the center it hits the first impedance wall 162 that provides pressure on the influent side and decreased pressure on the effluent side. The impedance structure 160A in this embodiment is centered between said first hollow barb and said second hollow barb and has a first vertical member 168 and a second vertical member 170. The two vertical members 168, 170 are parallel to each other. They 168, 170 terminate in a horizontal member 166 that closes the impediment structure 160A. On the other side of the impedance structure 160A is a second impedance wall 164 proximate the second side 114.

FIG. 6 illustrates an alternate structure to attain the same result. The impedance structure 160B has an impedance wall 176 that is centered between said first hollow barb and said second hollow barb that consists of a first side 172 proximate the first side 104 and a second side 174 proximate the second side 114 where the pressure is decreased.

The tubes 148, 150 can also be concentric with the cylindrical body 126, but this is not required. The two tubes 148, 150 share a common axis to minimize the obstruction within the cylindrical body 126, which is intended to minimize any reduction of air velocity through the internal cavity 136. With the air flow 140 through the internal cavity 136 at an adequate velocity, the first tube 148 has a higher pressure than the pressure in the cylindrical body 126 while the second tube 150 has a lower pressure than the pressure in the cylindrical body 126. The first tube 148 relies on principles similar to an air ram or Pitot tube whereas the second tube 150 relies principles similar to the Venturi effect.

A Pitot tube is a pressure measurement instrument used to measure fluid flow velocity. It is widely used to measure liquid, air and gas velocities in industrial applications. The Pitot tube is used to measure the local velocity at a given point in the flow stream and not the average velocity in the pipe or conduit. The Venturi effect is the reduction in fluid pressure that results when a fluid flows through a constricted section of pipe.

The air and ozone then pass through the second conduit 114 before passing through the backflow preventing safety device 106 after which the air and ozone pass through the third conduit 116 into the manifold 108 where the air and ozone 110 are dispersed into the water of the tub 112.

The discussion included in this patent is intended to serve as a basic description. The reader should be aware that the specific discussion may not explicitly describe all embodiments possible and alternatives that are implicit. Also, this discussion may not fully explain the generic nature of the invention and may not explicitly show how each feature or element can actually be representative or equivalent elements. Again, these are implicitly included in this disclosure. Where the invention is described in device-oriented terminology, each element of the device implicitly performs a function. It should also be understood that a variety of changes may be made without departing from the essence of the invention. Such changes are also implicitly included in the description. These changes still fall within the scope of this invention.

Further, each of the various elements of the invention and claims may also be achieved in a variety of manners. This disclosure should be understood to encompass each such variation, be it a variation of any apparatus embodiment, a method embodiment, or even merely a variation of any element of these. Particularly, it should be understood that as the disclosure relates to elements of the invention, the words for each element may be expressed by equivalent apparatus terms even if only the function or result is the same. Such equivalent, broader, or even more generic terms should be considered to be encompassed in the description of each element or action. Such terms can be substituted where desired to make explicit the implicitly broad coverage to which this invention is entitled. It should be understood that all actions may be expressed as a means for taking that action or as an element which causes that action. Similarly, each physical element disclosed should be understood to encompass a disclosure of the action which that physical element facilitates. Such changes and alternative terms are to be understood to be explicitly included in the description.

What is claimed is:

1. A system for introducing ozone into a blower plumbing system comprising:
   a vessel containing water to receive injected air;
   plumbing to disperse said air connected to said vessel;
   a blower that injects air to said plumbing;
   a backflow prevention device between a manifold and said blower that prevents flow from returning to said blower;
   a fitting placed between said blower and said backflow device that introduces ozone to be injected with said air, said fitting further comprising:
   a first side attachable to said blower;
   a second side attachable to said backflow prevention device;
   a center cylinder having an outer surface and an interior hollow portion between said first side and said second side;
   a first hollow barb attached to said outer surface of said center cylinder;
   a second hollow barb attached to said outer surface of said center cylinder wherein said first barb is proximate said first side and said second barb is proximate said second side and wherein said first barb and said second barb are oriented substantially perpendicular to said center cylinder;

an impeding structure centered between said first hollow barb and said second hollow barb in the interior hollow portion of said center cylinder;

influent tubing attached to said first hollow barb;

effluent tubing attached to said second hollow barb wherein said influent tubing and said effluent tubing attaches to an ozone generator thereby allowing said air to travel through said blower and perpendicular through said first barb into said ozone generator and back down through said effluent tubing into said second barb, through said backflow prevention device, through said plumbing into said vessel.

2. The system as defined in claim 1 wherein said fitting further comprises:

a first internal conduit inside said center cylinder extending from said first side wherein said first internal conduit has a diameter smaller than said center cylinder and wherein said first internal conduit carries influent up said first hollow barb;

a second internal conduit inside said center cylinder extending toward said second side wherein said second internal conduit has a diameter smaller than said center cylinder and wherein said second internal conduit carries effluent from said second hollow barb.

* * * * *